United States Patent
Smith (10) Patent No.: US 11,782,050 B2
(45) Date of Patent: Oct. 10, 2023

(54) CELL-BASED ASSAY FOR QUANTIFYING THE POTENCY AND EFFICACY OF CANNABINOIDS AND/OR TERPENOIDS, AND METHODS OF USE THEREOF

(71) Applicant: CannaMetrix, LLC, Rochester, NY (US)

(72) Inventor: Harold C. Smith, Rochester, NY (US)

(73) Assignee: CannaMetrix, LLC, Rochester, NY (US)

( * ) Notice: Subject to any disclaimer, the term of this patent is extended or adjusted under 35 U.S.C. 154(b) by 596 days.

(21) Appl. No.: 16/648,057

(22) PCT Filed: Sep. 18, 2018

(86) PCT No.: PCT/US2018/051569
§ 371 (c)(1),
(2) Date: Mar. 17, 2020

(87) PCT Pub. No.: WO2019/060316
PCT Pub. Date: Mar. 28, 2019

(65) Prior Publication Data
US 2020/0264163 A1  Aug. 20, 2020

Related U.S. Application Data (60) Provisional application No. 62/560,646, filed on Sep. 19, 2017.

(51) Int. Cl.
| | |
|---|---|
| *G01N 33/50* | (2006.01) |
| *C12N 9/22* | (2006.01) |
| *C12N 15/113* | (2010.01) |
| *G01N 33/94* | (2006.01) |

(52) U.S. Cl.
CPC ........... *G01N 33/5008* (2013.01); *C12N 9/22* (2013.01); *C12N 15/113* (2013.01); *G01N 33/5044* (2013.01); *G01N 33/5067* (2013.01); *G01N 33/94* (2013.01); *C12N 2310/20* (2017.05); *C12N 2800/80* (2013.01)

(58) Field of Classification Search
CPC .......... G01N 33/5008; G01N 33/5044; G01N 33/5067; G01N 33/94; C12N 9/22; C12N 15/113; C12N 2310/20; C12N 2800/80
USPC .......................................................... 435/29
See application file for complete search history.

(56) References Cited

FOREIGN PATENT DOCUMENTS

| | | | |
|---|---|---|---|
| WO | WO 1997/048820 A1 | 12/1997 | |
| WO | WO 2006/050214 A2 | 5/2006 | |
| WO | WO 2014/131114 A1 | 9/2014 | |
| WO | WO 2015/089487 A1 | 6/2015 | |

OTHER PUBLICATIONS

Zhu et al. Development of a universal high-throughput calcium assay for G-protein-coupled receptors with promiscuous G-protein Gα15/16. Acta Pharmacol Sin Apr. 2008; 29 (4): 507-516. (Year: 2008).*

Kampa-Schittenhelm et al. Dronabinol has preferential antileukemic activity in acute lymphoblastic and myeloid leukemia with lymphoid differentiation patterns. BMC Cancer (2016) 16:25 (12 pages + Figure S9). (Year: 2016).*

Hazekamp A. Cannabis Review. Department of Plant Metabolomics, Leiden University, Leiden, The Netherlands, 2008-2009 (98 pages). (Year: 2009).*

International Preliminary Report on Patentability issued in International Patent Application No. PCT/US2018/051569, dated Apr. 2, 2020.

International Search Report issued in International Patent Application No. PCT/US2018/051569, dated Feb. 13, 2019.

Gennequin, et al., "CRISPR/Cas-induced Double-Strand Breaks Boost the Frequency of Gene Replacements for Humanizing the Mouse Cnr2 Gene," *Biochemical and Biophysical Research Communication*, vol. 441, pp. 815-819 (2013).

Zhu, et al., "Development of a Universal High-Throughput Calcium Assay for G-protein-coupled Receptors with Promiscuous G-protein Galpha15/16," *Acta Pharmacol. Sin.*, vol. 29, No. 4, pp. 507-516 (Apr. 2008).

Debruyne, et al., "Emerging Drugs of Abuse: Current Perspectives on Synthetic Cannabinoids," *Subst. Abuse Rehabil.*, vol. 6, pp. 113-129 (Oct. 2015).

Fu et al., "Comparison of Immunological Characteristics of Mesenchymal Stem Cells Derived from Human Embryonic Stem Cells and Bone Marrow," *Tissue Eng. Part A*, vol. 21, No. 3-4, pp. 616-626 (Jan. 2015).

Shah, et al., "Contactin Associates with Sodium Channel Nav1.3 in Native Tissues and Increases Channel Density at the Cell Surface," *J. Neurosci.*, vol. 24, No. 33, pp. 7387-7399 (Aug. 2004).

Kulig, "Interpretation of Workplace Tests for Cannabinoids," *J. Med. Toxicol.*, vol. 13, No. 1, pp. 106-110 (Sep. 2016).

Russo, "Cannabidiol Claims and Misconceptions," *Trends Pharmacol. Sci.*, vol. 38, No. 3, pp. 198-201 (Jan. 2017).

Ueda, et al., "G Protein Beta Gamma Subunits. Simplified Purification and Properties of Novel Isoforms," *J. Biol. Chem.*, vol. 269, No. 6, pp. 4388-4395 (Feb. 1994).

Ho, et al., "Coupling of the expressed cannabinoid CB1 and CB2 receptors to phospholipase C and G protein-coupled inwardly rectifying K+ channels," Recept. Channels, vol. 6(5), pp. 363-374 (1999).

Fernandez-Lopez, et al., "Cannabinoids: Well-Suited Candidates for the Treatment of Perinatal Brain Injury," *Brain Sci.*, vol. 3, pp. 1043-1059 (2013).

Schmidt, et al., "Synthesis of an arrayed sgRNA library targeting the human genome," *Scientific Reports*, 10 pages (Oct. 2015).

Russo, "Beyond Cannabis: Plants and the Endocannabinoid System," *Trends Pharmacol Sci.*, vol. 37(7), pp. 594-605 (Jul. 2016).

(Continued)

*Primary Examiner* — Yih-Horng Shiao
(74) *Attorney, Agent, or Firm* — Foley & Lardner LLP (57) ABSTRACT

The present disclosure relates to, inter alia, cell-based assays, recombinant cell lines, and methods for quantifying the potency and efficacy of cannabinoids and/or terpenoids.

34 Claims, 6 Drawing Sheets
Specification includes a Sequence Listing.

(56) References Cited

OTHER PUBLICATIONS

Ligresti, et al., From phytocannabinoids to cannabinoid receptors and endocannabinoids: pleiotropic physiological and pathological roles through complex pharmacology, *Physiol. Rev* 96: pp. 1593-1659, (Sep. 2016).

Clapham, et al., G Protein beta gamma subunits, Annual Review of Pharmacology and Toxicology, 37, pp. 167-203 (Apr. 1997).

Kolesnikov, et al., "G-protein betagamma-complex is crucial for efficient signal amplification in vision," *The Journ. of Neuroscience*, vol. 31, pp. 8067-8077 (Jun. 2011).

Ibsen, et al., Cannabinoid $CB_1$ and $CB_2$ Receptor Signaling and Bias, Cannabis and Cannabis Research 2, pp. 48-60 (2017).

Offermanns, et al., G alpha 15 and G alpha 16 couple a wide variety of receptors to phospholipase C., J. Biol. Chem., vol. 270, pp. 175-180 (1995).

Ahn, et al., Distinct Roles of β-Arrestin 1 and β-Arrestin 2 in ORG27569-induced Biased Signaling and Internalization of the Cannabinoid Receptor 1 (CB1), *Jour. of Biol. Chem.*, vol. 288, No. 14, pp. 9790-9800 (Apr. 2013).

Hsieh, et al., "Internalization and Recycling of the CB1 Receptor," J. Neurochem, vol. 73, pp. 493-450 (1999).

Bennett, et al., "Nuclear Exclusion of the HIV-1 Host Defense Factor APOBEC3G Requires a Novel Cytoplasmic Retention Signal and is Not Dependent on RNA Binding." *J. Biol. Chem.*, vol. 283, pp. 7320-7327 (Mar. 2008).

Bennett, R.P., et al., (2006) "APOBEC-1 and AID are Nucleocytoplasmic Trafficking Proteins but APOBEC3G Cannot Traffic." *Biochem Biophys Res. Commun.*, vol. 350, No. 1, pp. 214-219 (Nov. 2006).

Galloway, et al., "APOBEC-1 Complementation Factor (ACF) forms RNA-Dependent Multimers," *Biochem. Biophys, Res. Commun.*, vol. 398, pp. 38-43 (Jun. 2010).

Miller, H.J. et al., "The Dimerization Domain of HIV-1 Viral Infectivity Factor Vif is Required to Block Virion Incorporation of APOBEC3G." *Retrovirology* 4, pp. 81-91 (Nov. 2007).

Bennett, R.P., et al., "An Analog of Camptothecin Inactive Against Topoisomerase I is Broadly Neutralizing of HIV-1 through Inhibition of Vif-dependent APOBEC3G Degradation," *Antiviral Res.*, vol. 136, pp. 51-59 (Dec. 2016).

Nguyen, et al., "Beta-arrestin-2 regulates cannabinoid $CB_1$ receptor signaling and adaptation in a CNS region-dependent manner." *Biol. Psychiatry*, vol. 71, pp. 714-724 (2012).

\* cited by examiner

SEQUENCE LISTING

```
<160> NUMBER OF SEQ ID NOS: 8

<210> SEQ ID NO 1
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 1
```
guuaugaagu cgauccuaga                                              20

<210> SEQ ID NO 2
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 2
ugguaucugc aaggccaucu                                              20

<210> SEQ ID NO 3
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 3
ugcggaaggu gguaucugca                                              20

<210> SEQ ID NO 4
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 4
aguggugaug gugcggaagg                                              20

<210> SEQ ID NO 5
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 5
ucacccagca uuccuccaug                                              20

<210> SEQ ID NO 6
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 6
ugucacccag cauuccucca                                              20

<210> SEQ ID NO 7
<211> LENGTH: 20
<212> TYPE: RNA
<213> ORGANISM: Artificial sequence
<220> FEATURE:
<223> OTHER INFORMATION: Synthetic sequence: Targeting Domain

<400> SEQUENCE: 7
cccaccccau ggaggaaugc                                              20

<210> SEQ ID NO 8
<211> LENGTH: 20
<212> TYPE: RNA
<213> ORGANISM: Artificial sequence

```
<220> FEATURE:
<223> OTHER INFORMATION: Synthetic sequence: Targeting Domain

<400> SEQUENCE: 8
ccaccccaug gaggaaugcu                                              20
```

CELL-BASED ASSAY FOR QUANTIFYING THE POTENCY AND EFFICACY OF CANNABINOIDS AND/OR TERPENOIDS, AND METHODS OF USE THEREOF

CROSS REFERENCE TO RELATED APPLICATIONS

This application is a U.S. National Phase filing under 35 U.S.C. § 371 of International Application No. PCT/US2018/051569, filed Sep. 18, 2018, and published as WO 2019/060316-A1 on Mar. 28, 2019, which claims priority benefit of U.S. Provisional Patent Application Serial No. 62/560,646, filed Sep. 19, 2017, the disclosures of which are hereby incorporated by reference herein in their entirety.

FIELD OF THE INVENTION

The present disclosure relates to, inter alia, cell-based assays, recombinant cell lines, and methods for quantifying the potency and efficacy of cannabinoids and/or terpenoids.

BACKGROUND OF THE INVENTION

Medicinal use of marijuana in plant form or *cannabis*-derived medicinal products or synthetic cannabinoids is rapidly gaining acceptance as a viable treatment to alleviate symptoms associated with chronic diseases that will soon become a primary treatment for disease. Currently, growing marijuana and the production and distribution of medicinal products has limited standardization and limited industry wide coordination partly because it has not been made uniformly legal across the 50 states. FDA approval for cannabinoid products in medical indications remains a future consideration. In this regulatory void, the quality of *cannabis* products and the determination of appropriate dose and perceptions of product efficacy are evaluated subjectively or at best semi-quantitatively. A few companies have begun to spring up with varying capacities to evaluate the concentration of 9 delta tetrahydrocannabinol (9$\Delta$THC), and other cannabinoids most commonly cannabidial (CBD) and cannabinol (CBN), select terpinoids as relative percent composition as well as testing for pesticides, herbicides, heavy metals and moisture content. An assessment of microbial or pesticide and other contaminates in smokable or edible *cannabis* products is an important service for safety but does not determine potency. In some cases, validation of the plant source (genetic typing) also may be provided which is of value in marketing specific products but again does not determine potency because the conditions plants are grown under markedly determine their cannabinoid and terpenoid chemical composition.

In the next few years, medical marijuana and cannabinoid products will have the public demand that will drive policy toward broadly recognizing the significant therapeutic potential *cannabis* can have in human disease management. In response, there will be a demand for quantitative metrics of potency and efficacy. Upon Federal approval, the industry has a multibillion dollar potential. A critical determinant of this success will be that *cannabis* products achieve the level of credibility that other drugs have when they go through FDA regulatory process, i.e., requiring testing and validation to ensure drug quality, mechanism of action, drug-target interaction validation, and the assessment of these attributes in product batch-to-batch consistency, product stability and potency upon processing, packaging and storage.

Medically relevant, biological endpoints have not been adopted by the industry as metrics for validating the quality and potency of *cannabis* products and ensuring batch-to-batch consistency. The industry has remained focused on quantifying product content of 9$\Delta$THC, CBD and CBN at the time the product was initially prepared without fully understanding how human cells in the body react to the product that patients will experience as the medicinal effect. In fact, cannabinoids trigger their drug-like responses due to the presence of a receptor-signaling system present in most cells of tissues in the human body. This endogenous system (the endocannabinoid system) is comprised of cell surface receptors that bind to cannabinoids and transduce a cellular response in a dose- and potency-dependent manner that may entail changes in cell metabolism, cell-to-cell communication, ion channel activity, gene expression, cell growth or cell death. The cellular response entails producing de novo cannabinoids derived from cellular membrane lipids (endocannabinoids), and these endogenous compounds are the purveyors of signals that change cell function in tissues throughout the body that is referred to as the potency and efficacy of the medicinal *cannabis* product. Different cell types, in different tissue throughout the human body vary in the endocannabinoid signaling pathways they use and hence the cell surface receptors and targeted cellular processes affected by plant, synthetic or endocannabinoids are not the same throughout the body. Because the biological response to cannabinoids is tissue-specific, the potency and efficacy of *cannabis* products cannot be assessed simple by quantifying the product's chemical composition of 9$\Delta$THC, CBD and CBN. The quantification of plant chemistries is important, but only becomes biomedically relevant in the context of human cell-based testing where the endocannabinoid system is activated in a community of human cells where potency and efficacy can be quantified relative to each cannabinoid product and the dose-response of these products.

The present invention is directed toward overcoming these and other deficiencies in the art.

SUMMARY OF THE INVENTION

The present invention relates to, inter alia, cell-based assays, recombinant cell lines, kits, and methods for quantifying the potency and efficacy of cannabinoids and/or terpenoids, including those found in *Cannabis* plants, humans, and animals, as well as in any synthetic analogs thereof.

In one aspect, the present invention relates to an assay for quantifying the potency and/or efficacy in dose-dependent cellular response to one or more cannabinoid and/or terpenoid, alone or in combination. In one embodiment, the assay comprises: (a) a microplate comprising an array of microwells containing one or more human cell types representing different human tissues; and optionally (b) reagents/components for quantifying the potency and/or efficacy of the one or more cannabinoid and/or terpenoid based on G protein-coupled receptor (GPCR) dependent signaling relative to a specific cannabinoid or terpenoid known to evoke signaling through the endocannabinoid system that will be used as a standardization and calibration control for the microplate assay relative to test compounds being evaluated.

In another aspect, the present invention relates to human cell lines for use in quantifying the potency and/or efficacy of one or more cannabinoid and/or terpenoid, alone or in combination. In one embodiment, the human cell lines comprise human cells engineered to express either human CB1 or CB2 (or chimeric proteins thereof) and a promiscuous recombinant human beta/gamma subunit that enable the otherwise suppression of calcium release by CB receptors to be a stimulation of calcium release due to cannabinoid signaling as determined through changes in the fluorescence intensity from a calcium sensitive fluorescent reagents.

In another aspect, the present invention relates to a kit for quantifying the potency and/or efficacy of one or more cannabinoid and/or terpenoid, alone or in combination. In one embodiment, the kit comprises: (a) a plurality human cell lines described herein; (b) optionally a microplate comprising an array of microwells for receiving the human cell lines; and (c) instructions on how to use one or a plurality of human cell lines in the assay for quantifying the potency and/or efficacy in cellular response to one or more cannabinoid and/or terpenoid, alone or in combination.

In another aspect, the present invention relates to a method for quantifying the potency and/or efficacy of one or more cannabinoid alone or in combination. In one embodiment, the method includes the steps of: (a) providing an assay and/or kit as described herein; (b) introducing one or more cannabinoid, either alone or in combination in cell cultures, over a range of doses into each of the test microwells; and (c) quantifying the potency and/or efficacy of the one or more cannabinoid based on G protein-coupled receptor (GPCR) dependent changes as a dose-response assay method.

Figure 1:
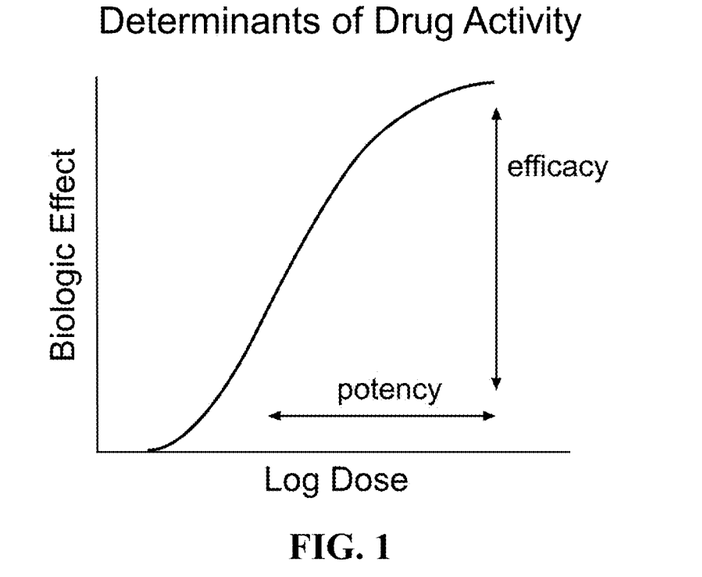
FIG. 1 is a graphic showing determinants of drug activity, i.e., potency and efficacy.

As used herein and as understood in the pharmaceutical industry, "potency" (as shown in the FIG. 1) is an expression of the activity of a drug in terms of the concentration or amount of the drug required to produce a defined effect, whereas clinical "efficacy" assesses the therapeutic effectiveness of the drug in humans. Potency and efficacy are not the same and can vary for different chemical analogs, from batch-to-batch and over the course of time following preparation (stability), but importantly can vary with the cell-type tissue-type and between patients. For purposes of the present disclosure, it is important to note that potency in the pharmaceutical definition is only relevant to 9ΔTHC for its psychotropic effect because the effects produced in the body for most of the chemical constituents of *cannabis* are not known at this time. The emerging *cannabis* industry is focused on potency of *cannabis* strains, extracts and products applied to the body, eaten or smoked. In this industry potency is equated to the amount of 9ΔTHC in the product. While it is true that the percent 9ΔTHC in products is equitable to the intensity of psychotropic effect (the high), the potency of 9ΔTHC or other cannabinoids or terpenoids for any other cellular response treatment or application have not been scientifically proven. So, current practice of using physical methods to separate and quantify the select cannabinoids and terpenoids is done to satisfy accepted practice but holds little to no medical meaning in terms of the non-psychotropic medicinal reasons a patient may seek treatment with *cannabis*. Current potency assurance standards therefore cannot quantify nor anticipate the potency *cannabis* products will have because they do not take into account the constellation of chemistries that contact cells of the body and collectively act to modulate the endocannabinoid response. Only cell-based methods can quantify the potency of *cannabis* products.

The significant change brought to this industry through the introduction of the presently disclosed cell-based methods for quantifying and validating potency and efficacy becomes clear in understanding the system in place throughout the cells of a human body that enable a response to *cannabis*. This is the endocannabinoid system which responds to cannabinoids and other small molecules by releasing internally and into the surrounding space small molecules that the cells produce from their lipids (endocannabinoids). The efficacy of plant or synthetic cannabinoids is therefore a result of how potent they are in eliciting endocannabinoid release. In persons consuming *cannabis* products, the efficacy of these products is related to and proportional to the endocannabinoid response of each cell type that interacts with the collective cannabinoid and terpenoid in *cannabis* products and whose numerous and varied receptors determine the potency intended as the medicinal effect and value to the patient. The efficacy of a *cannabis* product and its potency can only be reliably quantified from the response of cells in cell-based assays as described in this application.

The present disclosure improves on the prior art in addressing the deficiencies of inferring potency of a product such as a cannabinoid or terpenoid solely from a *Cannabis* plant chemical composition. For example, the present disclosure provides assays, recombinant cell lines, kits, and methods that addresses these deficiencies in the current state of testing by quantifying the biological efficacy of any and all chemistries from the *Cannabis* plant or synthetic chemistries as a result of the cellular endocannabinoid system naturally present in different human cells but differing in their response to phytocannabinoids or synthetic compounds in ways that cannot be known by only measuring and quantifying the chemistry in *Cannabis* products and making assumptions of efficacy and potency that may result when placed in contact with cells or tissues in the human body.

These and other objects, features, and advantages of this invention will become apparent from the following description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

DESCRIPTION OF THE INVENTION

The present invention relates to, inter alia, cell-based assays, recombinant cell lines, kits, and methods for quantifying the potency and efficacy of cannabinoids and/or terpenoids, including those found in *Cannabis* plants, humans, animals, and any synthetic derivatives thereof.

Provided herein are methods that will transform the medicinal *cannabis* industry with pharmaceutical standards for product quality and consistency based on dose-dependent, cell-based testing to determine potency and efficacy as a service for testing referred to as $EC_{50}$Reporter™ (single cell line) and $EC_{50}$Array™ (multiple cell lines) assay systems.

The technology will be useful to address this unmet need by determining 'the measured response' to cannabinoids through scientific testing based on the metrics of biological endpoints and a proprietary CB receptor signaling, reporter cell line to establish product quality and consistency. The technology disclosed herein will be a leading tool in this burgeoning global industry as a new quality assurance metric of scientifically validated products using defined biological endpoints.

The present disclosure provides a live cell approach and methods that establish a higher bar for product validation, quality assurance, batch-to-batch potency validation through the use of cell-based assays, proprietary cell lines and comprehensive product composition testing. The technology described herein is paradigm shifting for establishing medicinal *cannabis* product efficacy and potency (FIG. 1) in human cells rather than current practice of making inferences of product potency based on inferences from chemical quantification of plants and plant extracts. The direct assessment of efficacy and potency in human cells can transform business client, physician, and patient confidence in the health benefit and product performance reproducibly that can be anticipated from medicinal *cannabis*.

In one aspect, the present disclosure provides a cell-based assay for quantifying the potency and/or efficacy in cellular response to one or more cannabinoid and/or terpenoid, alone or in combination.

In one embodiment, the assay includes: (a) a microplate comprising an array of microwells containing genetically altered human cell types representing one or more different human tissues; and optionally (b) reagents/components for quantifying the potency and/or efficacy of the one or more cannabinoid and/or terpenoid based on G protein-coupled receptor (GPCR) dependent changes.

In one embodiment of the assay, the array is arranged so that microwells representing the same type of tissue are arranged in one or more row.

In one embodiment of the assay, the one or more rows have a sufficient number of microwells to enable escalating dosage analysis in triplicate of a test substance such as would be necessary to determine the half maximal effective dose or $EC_{50}$ of the one or more cannabinoid and/or terpenoid as it specifically relates to each different human cell type.

Various different human cell types can be used in the assay, including, without limitation, human cell types representing skin tissue, gastrointestinal tissue, immune tissue, liver tissue, neuronal tissue, bone tissue, muscle tissue, skin or theoretically any cell type that expresses the endocannabinoid system that may be of interest as a drug target treating disease.

In one embodiment of the assay, the human cell type is representing skin tissue and is A549.

In one embodiment of the assay, the human cell type is representing gastrointestinal tissue and is Caco-2.

In one embodiment of the assay, the human cell type is representing immune tissue and is H9.

In one embodiment of the assay, the human cell type is representing liver tissue and is HepG2.

In one embodiment of the assay, the human cell type is representing kidney tissue and is Nav1.3.

In one embodiment of the assay, the human cell type is representing neuronal tissue and is NGP.

In one embodiment of the assay, the human cell type is representing bone tissue and is U2OS.

In one embodiment of the assay, the human cell types derived from human biopsied tissues selected from the group consisting of skin tissue, gastrointestinal tissue, immune tissue, liver tissue, neuronal tissue, bone tissue, muscle tissue, or theoretically any cell type that expresses the endocannabinoid system that may be of interest as a drug target treating disease.

In one embodiment of the assay, the GPCR-dependent changes are selected from the group consisting of changes in intracellular calcium concentration, intracellular inositol phosphate accumulation, cannabinoid receptor internalization from the plasma membrane (CB1 or CB2 endocytosis), arrestin binding to GPCR, ERK/MAPK signaling, changes in protein phosphorylation and cannabinoid receptor redistribution in the treated cell.

In one embodiment of the assay, the microplate further comprises control microwells for use as controls.

In one embodiment, the control microwells contain the same cells as those in the *cannabis* product treated well but are treated with a known cannabinoid with predictable cellular response as a calibration control for comparison with the parallel well treated with the test material.

In one embodiment, the $EC_{50}$ response to the control treatment to standardize cell endocannabinoid responses will be used for comparing to the test substance $EC_{50}$ and by these means normalizing cellular responses being evaluated for one or more test substances being evaluated and used to normalize different cellular endocannabinoid responses to similar test substances (e.g. Normalized test substance potency=$EC_{50test\ substance}$ divided by $EC_{50standard\ compound}$).

In one embodiment, the one or more cannabinoid is selected from the group consisting of a phytocannabinoid, an endocannabinoid, and a synthetic cannabinoid.

In one embodiment, wherein the phytocannabinoid is selected from the group consisting of tetrahydrocannabinols (9ΔTHC), cannabidial (CBD), and cannabinol (CBN).

In one embodiment, the standard control or endocannabinoid is selected from the group consisting of ω-6 endocannabinoid (eCB), anandamide (N-arachidonoylethanolamide), and 2-arachidonoylglycerol (2-AG).

In one embodiment, the synthetic cannabinoid is selected for testing or as the standard control from the group consisting of ACEA (CB1 agonist>>CB2), AM251 (CB1 antagonist>>CB2), JWH133 (CB2 agonist>>CB1), and AM630 (CB2 antagonist>>CB1).

In one embodiment, the cannabinoid is in the form of a formulation selected from the group consisting of Marinol (9Δ THC analog), Syndros (THC analog), Casemet (THC analog), Satevex (9Δ THC, CBD, CBN extract), and NY State Tixtures (20 9ΔTHC:1CBD, 1 9ΔTHC:1CBD, and 1 9ΔTHC:20 CBD).

In one embodiment, the terpenoid is selected from the group consisting of camphene, D3 carene, limonene, and myrcene.

In another aspect, the present disclosure provides a human cell line for use in quantifying the potency and/or efficacy of one or more cannabinoid and/or terpenoid, alone or in combination, said human cell line as disclosed and/or contemplated herein.

In one embodiment, the cell line comprises human cells engineered to express either human CB1 or CB2 (or chimeric proteins thereof) and a promiscuous recombinant human beta/gamma subunit that enable the otherwise suppression of calcium release by CB receptors to be a stimulation of calcium release due to cannabinoid signaling.

In a further aspect, the present disclosure provides a kit for quantifying the potency and/or efficacy of one or more cannabinoid and/or terpenoid, alone or in combination, said kit comprising the components as disclosed and/or contemplated herein.

In one embodiment, the kit includes: (a) a plurality of human cell lines as described and/or contemplated herein; (b) optionally a microplate comprising an array of microwells for receiving the genetically altered human cell lines; (c) instructions on how to use the plurality of human cell lines for use as an assay for quantifying the potency and/or efficacy in cellular response to one or more cannabinoid and/or terpenoid, alone or in combination; and (d) calcium concentration sensitive, cell permeable fluorescent chemistry.

In another aspect, the present disclosure provides a method for quantifying the potency and/or efficacy of one or more cannabinoid and/or terpenoid, alone or in combination, said method comprising the steps as disclosed and/or contemplated herein.

In one embodiment, the method includes the steps of: (a) providing an assay or a kit as disclosed and/or contemplated herein; (b) introducing one or more cannabinoid and/or terpenoid, either alone or in combination, into each of the test microwells; and (c) quantifying the potency and/or efficacy of the one or more cannabinoid based on G protein-coupled receptor (GPCR) dependent increased of calcium in the treated cells as visualized by a calcium concentration-sensitive, cell permeable, fluorescent dye (e.g., dyacas9) added to the tissue culture media in each microwell.

In one embodiment, the method further includes performing the steps of: (a) thawing frozen cells of known number and adding them to the wells of microtiter plates in a concentration to cover the bottom of each well such that 60% of the cells are in direct contact with one another (60% confluency) in tissue culture media appropriate to the given cell type; (b) maintaining the cells for 12 to 24 hours to become adherent under cell growth conditions of temperature, humidity and $CO_2$ appropriate for each cell type; (c) diluting stock solutions of standard control and test substances by in half-log concentration steps from full strength concentration of the stock solutions over 7 dilutions appropriate for adding to the volume of tissue culture media in each well to achieve the desired final concentrations that cells are exposed to; (d) incubating the cells with standard for test substance as in Step (b) for varying durations ranging from minutes to hours; (e) adding calcium concentration-sensitive, cell permeable fluorescent dye of appropriate concentrations to each well and allowing reaction with cells for minutes to hours; (f) quantifying fluorescence due to calcium binding to the fluorescent chemistry by a plate reader at the appropriate excitation/emission light wavelengths; and (g) calculating $EC_{50}$ based on half maximal fluorescent signal in the seven dose-range assay for the standard control and test substance treatment groups and averaging the triplicates.

In one embodiment of the method, the *cannabis* control standard and test substance potency and $EC_{50}$ are quantified using discrete steps in the endocannabinoid signal systems where the cells have been engineered to express fluorescent CB1 or CB2 (chimeric proteins such as CB1-EGFP, CB2-EGFP) cannabinoid receptor whose internalization from the plasma membrane upon treatment of the cell is a dose-dependent response of the endocannabinoid system to cannabinoids.

In one embodiment of the method, the *cannabis* control standard and test substance potency and $EC_{50}$ are quantified using discrete steps in the endocannabinoid signal systems where the cells and have engineered to express arrestin and CB1 or CB2 as FRET (Forester Resonance Energy Transfer) pairs such as chimeric proteins CB1-EGFP and Arrestin-REACh2 or CB2-EGFP and Arrestin-REACh2 to cannabinoid induce intracellular translocation of arrestin and binding to GPCRs.

In one embodiment of the method, the *cannabis* control standard and test substance potency and $EC_{50}$ are quantified using discrete steps in the endocannabinoid signal systems where the cells and have engineered to express members of the ERK/MAPK pathway as FRET pairs as a reporter of potency of the cannabinoid substance activation of the endocannabinoid system.

In one embodiment of the method, the *cannabis* control standard and test substance potency and $EC_{50}$ are quantified using discrete steps in the endocannabinoid signal systems where the cells and have engineered to express reporter genes whose enhancers and promoters are responses to transacting gene transcription factors, such as for FAT, STAT or NFkB, as reporters of potency of the cannabinoid substance activation of the endocannabinoid system.

Certain Embodiments and Aspects of Features of the Disclosure

Provided below is a description of some specific embodiments or aspects of the present disclosure.

Figure 2:
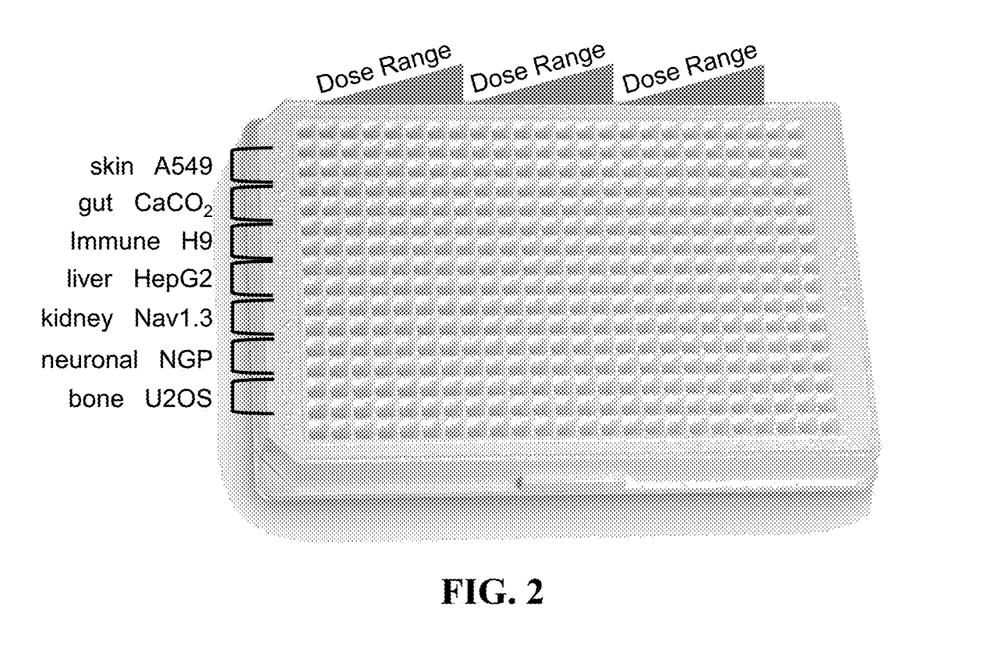
FIG. 2 is a schematic drawing of one embodiment of an 50% efficacy concentration ($EC_{50}$) array assay system of the present invention that tests one or more cell types from human tissues that have been genetically engineered for the purpose of quantifying *cannabis* product potency and efficacy.
Figure 3A:
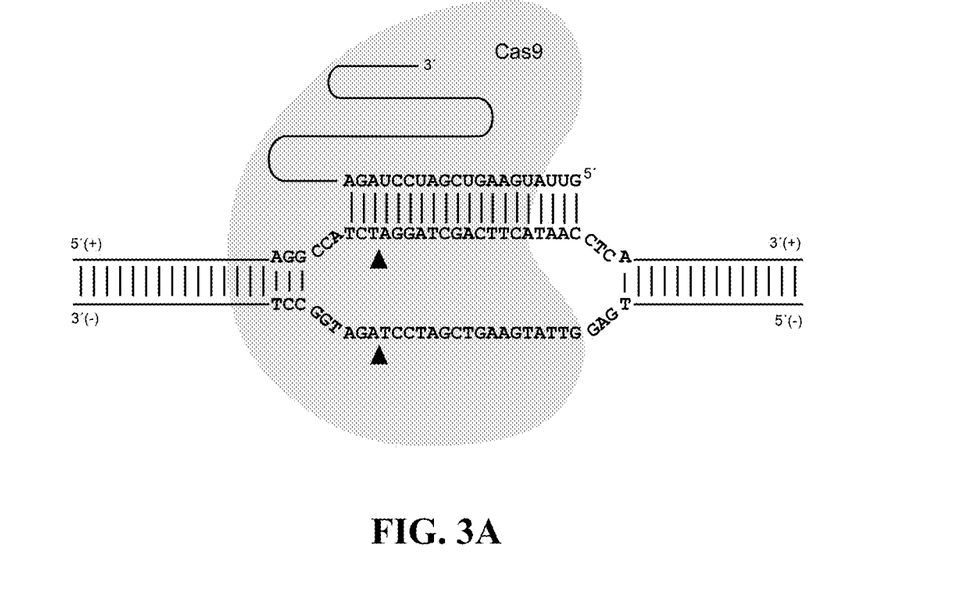
FIGS. 3A-3D are examples of gRNAs which can target cas9 for selective DNA cutting and knockout (KO) of CB1 while leaving CB2 expression intact and target the $CNR_1$ gene in the *Homo sapiens* genome. The gRNA in FIG. 3A creates a double stranded break at location 88,145,261 binding to the (+) strand. The gRNA in FIG. 3B creates a double stranded break at location 88,145,258 binding to the (−) strand. The gRNA in FIG. 3C creates a double stranded break at location 88,145,249 binding to the (−) strand. The gRNA in FIG. 3D creates a double stranded break at location 88,145,238 binding to the (−) strand.
Figure 3B:
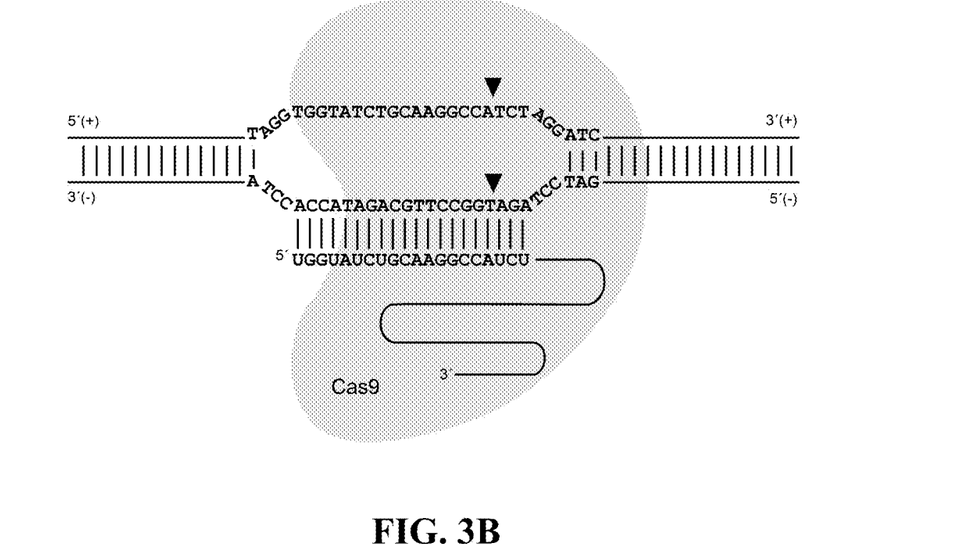
Figure 3C:
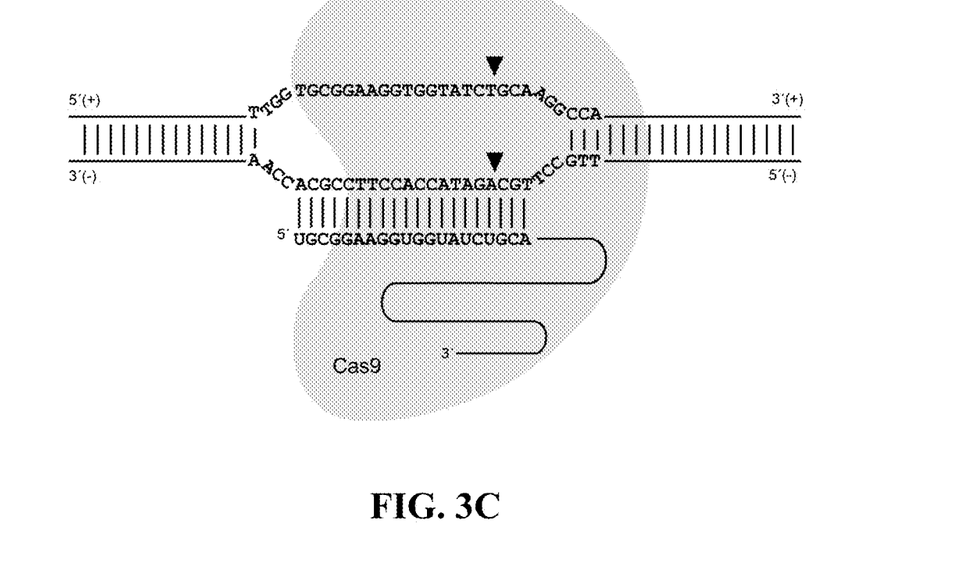
Figure 3D:
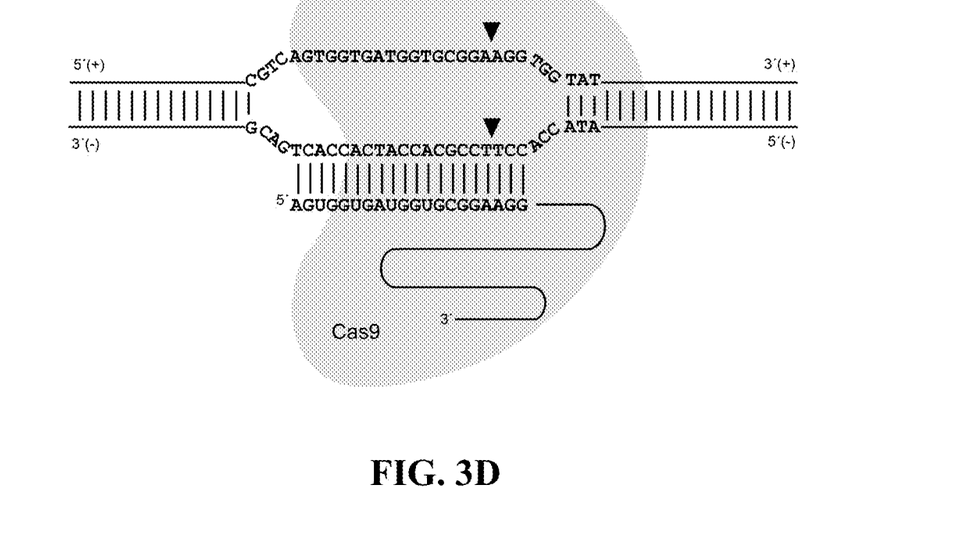
Figure 4A:
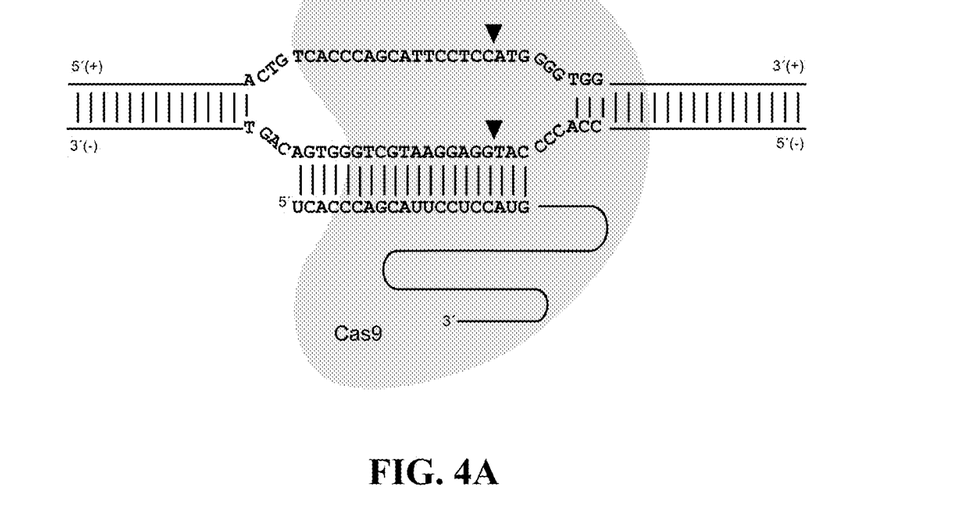
FIGS. 4A-4D are examples of gRNAs which can target cas9 for selective DNA cutting and KO of CB2 while leaving CB1 expression intact and target the $CNR_2$ gene in the *Homo sapiens* genome. The gRNA in FIG. 4A creates a double stranded break at location 23,875,616 binding to the (−) strand. The gRNA in FIG. 4B creates a double stranded break at location 23,875,614 binding to the (−) strand. The gRNA in FIG. 4C creates a double stranded break at location 23,875,609 binding to the (+) strand. The gRNA in FIG. 4D creates a double stranded break at location 23,875,608 binding to the (+) strand.
Figure 4B:
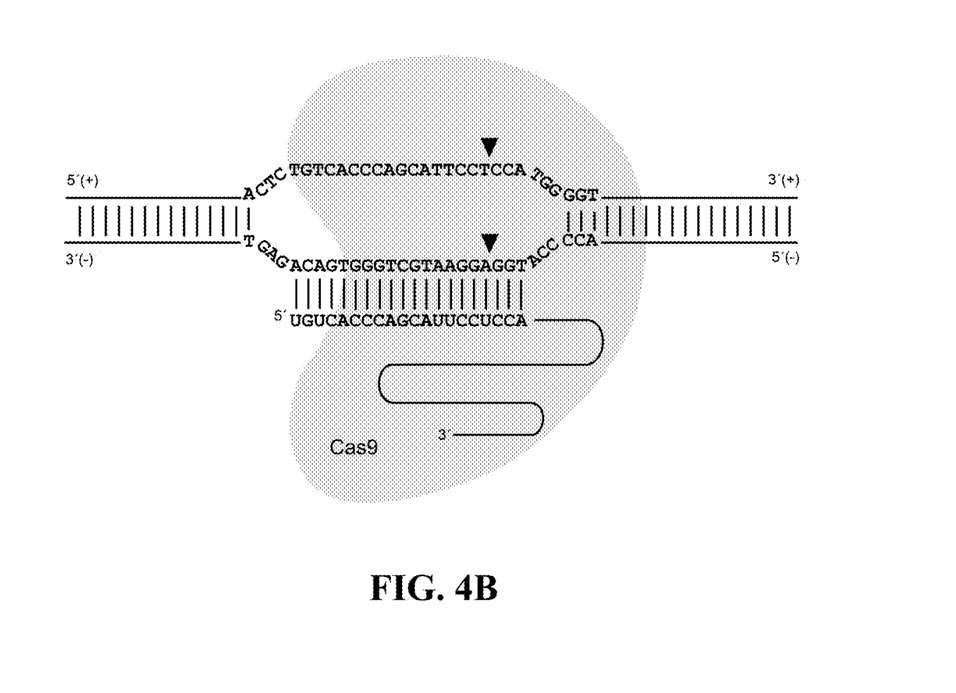
Figure 4C:
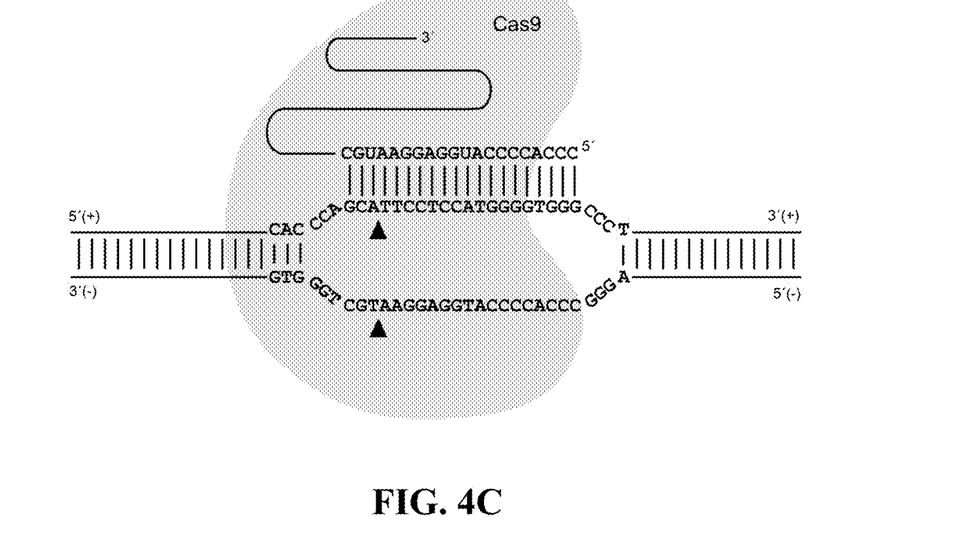
Figure 4D:
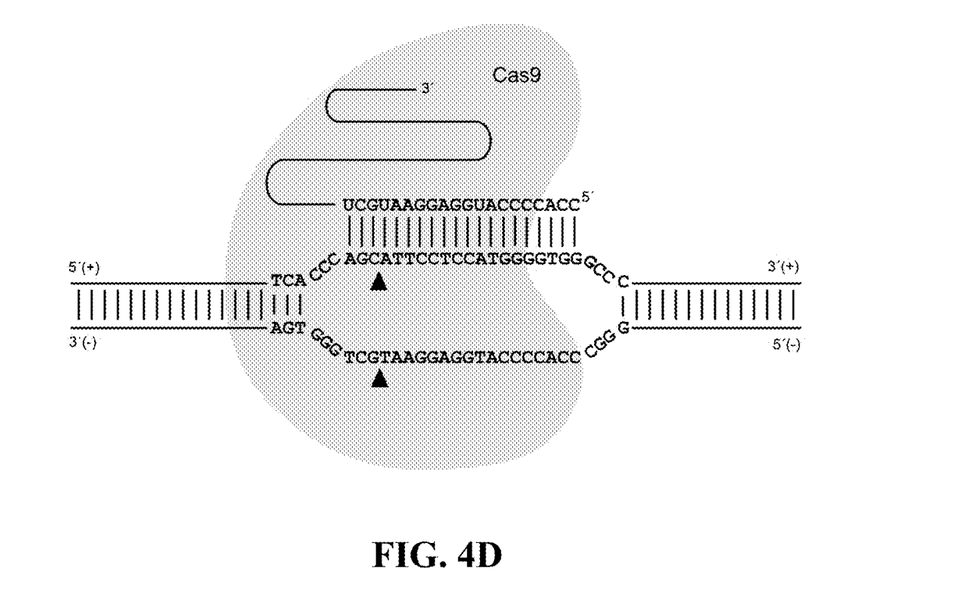

As shown in FIG. 2, in one embodiment, the present disclosure provides an assay/$EC_{50}$ array that can be used in a direct method for quantifying the potency of *cannabis* products based on GPCR-dependent changes in intracellular calcium concentration, intracellular inositol phosphate accumulation, cannabinoid receptor internalization from the plasma membrane (CB1 or CB2 endocytosis), arrestin binding to GPCR or signaling through the ERK/MAPK pathway. FIG. 2 illustrates a plate of arrayed human cell types representing different tissues in the body. Each cell type plated into the wells of the plate will be exposed to an escalation through seven doses of medicinal *cannabis* product relative to chemical or hormonal standard agonist and this dose-response set will be repeated for triplicate determinations. This is referred to as the CannaMetrix $EC_{50}$Array™ system and enables the reproducible assessment of *cannabis* product potency as a dose response and calculated $EC_{50}$ (effective dose at 50% of full stimulation) in cell types from tissues throughout the human body and all *cannabis* and terpenoid compounds thus capturing the potential medicinal value to the patient. Test-to-test reliability is ensured through ratiometric quantification responses to each dose of *cannabis* relative to that of a known agonist of the endocannabinoid system. Edge effects are avoided by omitting all of columns 1 and 24 and rows A and P.

The present disclosure includes a kit that contains one or more human cell lines engineered to express either human CB1 or CB2 (or chimeric proteins thereof) and/or a promiscuous recombinant human beta/gamma subunit that enable the otherwise suppression of calcium release by CB receptors to be a stimulation of calcium release due to cannabinoid signaling. In one embodiment, the kit includes a vial of frozen cells for each CB1 and CB2 engineered cells and instructions on their use.

In one embodiment, the recombinant cells in the kit can be prepared by first using CRISPR/cas9 to knock out CB1 and CB2 from a human cell lines such as U2OS or HEK293T. Thereafter, one could then clone in human CB1 or CB2 receptors that are coupled to the three subunits of GPCR with or without a chimeric protein such as EGFP (for the receptor trafficking in response to CB treatment) but importantly with human beta/gamma subunits that act promiscuously. The coupling of recombinant CB1 or CB2 (which are members of the $G_{i_o}$ receptors that inhibit calcium signaling) would be to G alpha 15. See, e.g., Ho et al., "Coupling of the expressed cannabinoid CB1 and CB2 receptors to phospholipase C and G protein-coupled inwardly rectifying K+ channels," *Receptors Channels* 6(5): 363-374 (1999). Additional downstream mediators of CB1 and CB2 signaling are known in the art. See, e.g., Fernández-López et al., "Cannabinoids: Well-Suited Candidates for the Treatment of Perinatal Brain Injury," *Brain Sci.* 3:1043-1059 (2013) (e.g., FIG. 2)

The present disclosure includes a cell-based method for quantifying the potency of phyto- or endocannabinoids, alone or in combination, synthetic or as complex mixtures or extracts of biologically produced compounds from plant sources.

The present disclosure also includes a method in which cannabinoids as in the above are placed in contact with live cells grown in vitro in a series of escalating dose treatments that quantify the dose-proportional cellular response to cannabinoid compounds (potency) in the calculation of the half maximal dose response or $EC_{50}$.

The present disclosure also includes a method in which said dosing is performed with human cells various organ and tissues containing cannabinoid receptors and endocannabinoid signaling pathways.

The cells can include, but not be limited to, the following cells that are either wild type or engineered for CB1 or CB2 knockouts, or chimeric proteins such as CB1-EGFP/CB2-EGFP and/or promiscuous recombinant human beta/gamma subunit in the background of: HEK293T, H9, U2OS, CaCO2, A549, HepG2, NGP, Nav1.3 or any other immortal or primary cell line.

The present disclosure also includes a method for determining the potency of cannabinoid compounds or products that evaluates simultaneous the calculated $EC_{50}$ of a specific cell types or from multiple cells from different tissues of the body as a measure of the response to cannabinoids throughout different tissues in the human body as the whole body medicinal potency.

The present disclosure also includes a method in which said human cells alone or as arrays have reporter systems made of particular genes cloned into these cells or chemistries added to them in culture that report on the potency of cannabinoid product as the ability of cannabinoid products to stimulate signaling through the endocannabinoid system within cells in a dose-dependent manner.

In accordance with the present disclosure, reporters can be used that reveal signaling through both immediate and secondary and dependent pathways that active or inhibit cellular processes necessary for metabolism, cell exocrine, paracrine autocrine hormonal release, cell growth or cell death.

As used herein, the methods of the present disclosure rely not only on the potency of cannabinoid products to bind to cell surface receptors but on a cellular network of pathways that lead to cellular responses in the release of endocannabinoids that promote reporter responses within the cell cultures tests and reflect potency of compounds being tested.

The present disclosure also includes a method inclusive of all the described methods wherein the cells tested represent those specifically involved in metabolism of sugars and lipids in response to cannabinoid potency.

The present disclosure also includes a method inclusive of all the described methods wherein the cells tested represent those specifically involved immune and inflammatory responses to cannabinoid potency.

The present disclosure also includes a method inclusive of all the described methods wherein the cells tested represent those that specifically represent cancer and neoplastic cells responses in cell growth or cell death to cannabinoid potency.

The present disclosure also includes a method inclusive of all the described methods wherein the cells tested represent those specifically involved neurological cell responses to cannabinoid potency.

The present disclosure also includes a method inclusive of all the described methods wherein the cells tested are obtained from a specific individual or individuals who seek to determine their individual cellular endocannabinoid system sensitivity to the potency of various cannabinoids or materials obtained from various sources or strains of marijuana.

Methods

Disclosed herein are methods for utilizing known and newly designed RNA guides (gRNAs) for gene targeting using either commercially available CRIPSR design tools and gRNA oligonucleotide synthesis or tools specifically designed to delineate specific cannabinoid by-products or minor active ingredients. The gRNAs for CB1 or CB2 are designed to select for appropriate complementarity within the 5' end of the CB1 or CB2 mRNAs' translation open reading frame within exon 2 and appropriately position PAM sequence (NNM) recognized by cas9 from *S. pyogenes*. Off-target complementarity to other genes was minimized, so as to avoid off-target gene editing, by validating CB1 and CB2 gRNAs did not bind to 304,792,603 off-target sequences. The gRNAs depicted in FIGS. 3A-3D and FIGS. 4A-4D will target cas9 for a selective DNA cutting and KO of CB1 while leaving CB2 expression intact (FIGS. 3A-3D), KO of CB2 while leaving CB1 expression intact (FIGS. 4A-4D) or double KO of both CB1 and CB2 while leaving other receptors for cannabinoids and terpenoids (referred to henceforth as the entourage receptors) intact.

CB1 gene knockout is accomplished by selecting one of the gRNAs in FIGS. 3A-3D for CB1 and transfecting it along with an expression plasmid encoding cas9 into a mammalian cell line of choice by the electroporation method for delivering into cells CRISPR/cas9 ribonucleoprotein complexes (RNP) assembled with a commercially available kit (Synthego) and culturing the so treated cells for 48-72 hours.

CB1 gene knockout is accomplished by selecting one of the gRNAs in FIGS. 3A-3D for CB1 and transfecting it along with an expression plasmid encoding cas9 into a mammalian cell line of choice by the electroporation method for delivering into cells CRISPR/cas9 ribonucleoprotein complexes (RNP) assembled with a commercially available kit (Synthego) and culturing the so treated cells for 48-72 hours. (See, Schimdt, T., et al. (2015) "Synthesis of an arrayed sgRNA library targeting the human genome," *Sci Reports* 5:14987.)

The purified genomic DNA can be bidirectionally sequenced by standard Sanger sequencing method (commercially available from GeneWiz) and deletions within exon 2 of the CB1 or CB2 gene confirmed using publicly available software for comparative sequence analysis. DNA sequencing confirms that >75% of the DNA sequenced (corresponding to >75% of the cell population) has an exon 2 genomic deletion (indel). To select a clonal KO cell line from the mixed cell population cells is plated by limiting dilution in 96-well microtiter dishes so that each well contains 1 or less cells. Following propagation of cells in each well as clones, genomic DNA and total cellular RNA are sequenced again to confirm that the cell lines have genomic KO of exon 2 and that fragments of CB1 or CB2 mRNAs are either not expressed or (due to the indel) cannot be translated by the cell into functional CB or CB1 proteins.

The gene edited and selected CB1 and CB2 cell lines are then grown in bulk and frozen in aliquots for future use.

It is at this stage that the CB1/CB2 double knockout cell line can be created and validated as described above by performing CRISPR for CB1 or CB2 in CB2- or CB1- knockout cell lines respectively.

Disclosed herein is a method for measuring and quantifying the amount of a cannabinoid in a sample, comprising measuring the intracellular calcium response when a cannabinoid receptor is contacted with a sample comprising one or more cannibinoids.

Intracellular Calcium Response

CB1 and CB2 are GPCR's which when in contact with 9ΔTHC or CBD (as examples) signal in a dose-dependent manner to macromolecules in the cell interior to activate biochemical pathways and gene expression to change the cells physiology and structure. The C-terminal protein of GPCR which is exposed to the cell interior, interacts with at least three proteins inside the cell: gamma, beta and alpha subunits that coalesce with the GPCR at the inner surface of the cell membrane. When ligands such as cannabinoids bind to the GPCR, such as CB1, CB2 or the entourage receptors, it causes a conformational change in the GPCR, which allows it to act as a guanine nucleotide exchange factor (GEF). The GPCR can then activate an associated G protein by exchanging the GDP bound to the G protein for a GTP. The G protein's α subunit, together with the bound GTP, can then dissociate from the β and γ subunits to further affect intracellular signaling proteins or target functional proteins directly depending on the α subunit type ($G_{\alpha s}$, $G_{\alpha i/o}$, $G_{\alpha q/11}$, $G_{\alpha 12/13}$).

The CB1 and CB2 are cell membrane spanning proteins of the G protein coupled receptor (GPCR) family of proteins that sense and bind to molecules exterior to the cell membrane, like *cannabis*, and structurally transducing this information to a network of signaling molecules and pathways inside the cell. Biochemical pathways linked to GPCR proteins regulate a variety of cell functions and structures from vision to metabolism to cell growth and differentiation. (See e.g. Russo, E. B. (2016) 'Beyond *Cannabis*: Plants and the Endocannabinoid System'. Trends in Pharmalogical Sciences 37:594-605; Pertwee, R. G. in *Handbook of Cannabis* (2016) Chapters 2, 3, 4 and 5 Oxford University Press, Oxford UK; Ligresti, A., De Petrocellis, L., and Di Marzo, V. (2016) 'From phytocannabinoids to cannabinoid receptors and endocannabinoids: pleiotropic physiological and pathological roles through complex pharmacology'. Physiol Rev 96: 1593-1659.

The CB1 and CB2 are cell membrane spanning proteins of the G protein coupled receptor (GPCR) family of proteins that sense and bind to molecules exterior to the cell membrane, like *cannabis*, and structurally transducing this information to a network of signaling molecules and pathways inside the cell. Biochemical pathways linked to GPCR proteins regulate a variety of cell functions and structures from vision to metabolism to cell growth and differentiation CB1 and CB2 are encoded by human genes CNR1 and CNR2 respectively on chromosomes 6q14-q15 and 1p36.11 respectively. CB1 protein has a molecular weight of 52,858 Daltons and CB2 has a molecular weight of 39,681 Daltons. The proteins are broadly expressed at various abundance throughout the tissues of the human body. The amino acid sequences and gene sequences of CB1 and CB2 are known. CB1 and CB2 have 40% amino acid sequence similarity. There is substantial differences in the gene sequence of CB1 and CB2 which enable selective CRISPR gene editing of each of these genes Activation of many GPCR stimulates the adenylate cyclase enzyme to produce a secondary signaling molecule known as cyclic adenosine mono-phosphate (cAMP) which promotes the release of calcium into the cells' cytoplasm from depots in the endoplasmic reticulum and mitochondria. The transient surge in free calcium within the cell's cytoplasm is proportional to the dose of the ligand and can be quantified by adding a commercially available vital dye (cell permeable and nontoxic) Fluro-4 that emits fluorescent light at 590 nm in response to irradiation with 480 nm light and in direct response to the amount of calcium available for Fluor-4 to bind. (See, Clapham, D. E., et al. (1997). "G protein beta gamma subunits". *Annual Review of Pharmacology and Toxicology.* 37: 167-203 and Kolesnikov, A. V., et al., (June 2011). "G-protein betagamma-complex is crucial for efficient signal amplification in vision". *The Journal of Neuroscience.* 31 (22): 8067-77.)

When cannabinoids bind to CB1 and CB2 they inhibit the production of cAMP and do not promote a surge of calcium release in the cytoplasm. Not all cannabinoids have a negative effect on the production of cAMP and the release of calcium and the signaling mechanism for many of the cannabinoid and terpenoid receptors responsible for the entourage effect are unknown. Even if all receptors involved in the entourage effect and plant compounds they respond to were known, it would be impractical to validate the potency of *cannabis* by testing these individually. The $EC_{50}$ array overcomes this road block to testing the potency of plant sourced material by converting all GPCR signaling to a positive cAMP production and calcium release through the genetic introduction of the stable expression of a promiscuous G alpha subunit 15 or G alpha 16 as cell lines. (See, Søes, I. M., et al., (2017) Cannabinoid $CB_1$ and CB2

Receptor Signaling and Bias. *Cannabis* and *Cannabis* Research 2:48-60 (Piomelli, D., ed) MaryAnn Libert Publishers.)

Commercially available cells in which the cannabinoid receptors have been engineered to express G alpha 15/16 when treated with Fluro-4 and *cannabis* will emit fluorescence at 590 nm following irradiation with 480 nM within seconds to minutes in a *cannabis* dose-dependent manner. Cells that have not been engineered with G alpha 15/16 (native base line control cells), when treated with Fluro-4 plus *cannabis* and irradiate with 480 nm light will have mixed signaling due to positive and negative effects on free calcium. Due to the mixed cannabinoid receptor responses, native base line control cells lacking G alpha 15/16 do not have fluorescent signals that are strong enough for the detection limits necessary for a robust dose-response evaluation of a product's potency. Fluorescent signals from the native base line control cells provide the fluorescence base line for optimizing the positive Fluro-4 fluorescent signal in G alpha 15/16 engineered and clonally selected cell lines. The cDNA clone for G alpha 15/16 (NM_002068) that will be used to engineer these cells is commercially available from Origene and is further engineered to have a V5 epitope tag added to the C- or N-terminus of the protein for ease of western blot detection during the selection and optimization of a stable cell line expressing G alpha 15/16. (See, Offermanns, S. et al., (1995) "G alpha 15 and G alpha 16 couple a wide variety of receptors to phospholipase C," *J. Boil. Chem.* 270:175-80.

The changes in 590 nm Fluro-4 fluorescent signals due to escalating concentrations of *cannabis* (the dose response) added to the cell culture media is quantified using a Fluormax spectrophotometer plate reader. From these data the concentration of *cannabis* that evokes a half maximal fluorescence in response or $EC_{50}$ is determined by plotting the data and identifying the mathematical first derivative of the dose response curve. The $EC_{50}$ determined using human cells with their natural *cannabis* receptors but stably expressing G alpha 15/16 is a measure of *cannabis* product's potency due to the totality of native receptor signaling. This $EC_{50}$ due to 'mixed' signaling is the minimum necessary approach (assay tool) for quantifying *cannabis* potency in human cells.

In keeping with the above disclosed assay approach for $EC_{50}$ determination of *cannabis* potency, the use of CB1 and CB2 CRISPR enables the dose response to be ascribed to receptor classes; a metric that correlates with the product's use indication and medicinal value. This has the utility of ruling in or ruling out signaling by *cannabis* products through CB1, CB2 or the entourage receptors when the indication, for example, might be to not evoke a psychotropic effect through CB1 signaling as might be desired for treatment indications such as epilepsy, appetite stimulation (wasting disorder) or immune modulation. CB1-CRIPSR cell $EC_{50}$ is the result of signaling by *cannabis* products through CB2 and the entourage receptors. CB2-CRISPR cell $EC_{50}$ is the result of signaling by *cannabis* products through CB1 and the entourage receptors. CB1/CB2-CRISPR cell $EC_{50}$ is the result of signaling by *cannabis* products only through the entourage receptors. From these data the signaling of *cannabis* products due exclusively through CB1 or CB2 can be calculated through equations #1 and #2 respectively:

$$EC_{50CB2-CRISPR} - EC_{50CB1/CB2-CRISPR} = EC_{50\ CB1} \qquad \#1:$$

$$EC_{50CB1-CRISPR} - EC_{50CB1/CB2-CRISPR} = EC_{50CB2} \qquad \#2:$$

Consequently, the presently disclosed $EC_{50}$ Report analysis of each *cannabis* product characterizes its potency in human cells based on three $EC_{50}$ values: $EC_{50CB1}$, $EC_{50CB2}$, $EC_{50entourage}$. The advantage of this direct assessment of *cannabis* product potency along specific receptor pathways is both in the assessment of *cannabis* products with high probability of specific desired medicinal effects and the assessment of the products stability in terms of its ability to stimulate specific receptor signaling from batch-to-batch, over time in storage and following different delivery methods (food, beverages, vapes or smoke).

As stated previously, the biological response to *cannabis* in CRISPR engineered cell lines is validated by testing escalating doses of individual cannabinoids known to bind to and signal through CB1 and/or CB2 that are available from the National Institutes of Health/National Institute for Drug Abuse. Table 1 contains a list of examples of test substances that can be used in validating fluorescence as a quantitative metric for *cannabis* dose-response and their affinity for CB1 and CB2.

TABLE 1

|  | $CB_1$ affinity ($K_i$) | Efficacy towards $CB_1$ | $CB_2$ affinity ($K_i$) | Efficacy towards $CB_2$ | Type |
|---|---|---|---|---|---|
| Anandamide | 78 nM | Full agonist | 370 nM | ? | Endogenous |
| N-Arachidonoyl dopamine | ? | Agonist | ? | ? | Endogenous |
| 2-Arachidonoylglycerol | ? | Full agonist | ? | ? | Endogenous |
| 2-Arachidonyl glyceryl ether | 21 nM | Full agonist | 480 nM | Full agonist | Endogenous |
| 4-9-Tetrahydrocannabinol | 10 nM | Partial agonist | 24 nM | Partial agonist | Phytogenic |
| EGCG | 33.6 µM | Agonist | >50 µM | ? | Phytogenic |
| Yangonin | 0.72 µM | ? | >10 µM | ? | Phytogenic |
| AM-1221 | 52.3 nM | Agonist | 0.28 nM | Agonist | Synthetic |
| AM-1235 | 1.5 nM | Agonist | 20.4 nM | Agonist | Synthetic |
| AM-2232 | 0.28 nM | Agonist | 1.48 nM | Agonist | Synthetic |
| UR-144 | 150 nM | Full agonist | 1.8 nM | Full agonist | Synthetic |
| JWH-007 | 9.0 nM | Agonist | 2.94 nM | Agonist | Synthetic |
| JWH-015 | 383 nM | Agonist | 13.8 nM | Agonist | Synthetic |
| JWH-018 | 9.00 ± 5.00 nM | Full agonist | 2.94 ± 2.65 nM | Full agonist | Synthetic |

$IC_{50}$ Endocytosis Reporter

As is true with most membrane receptors, CB1 and CB2 signaling strength is modulated by cells that have continually been exposed to *cannabis* by sequestering the receptors from the surface of cells to the interior of cells (a process known as receptor endocytosis). The effect is to limit the number of cell surface exposed receptors that can respond to *cannabis*. In a patient with continuous use of *cannabis* this has the effect of lowering the apparent effective dose necessary to obtain a desired outcome. Endocytosed receptors are eventually recycled inside the cell and returned to the surface without bound *cannabis*; enabling the patient to regain their sensitivity to the original *cannabis* dose response over time. Not all cannabinoids have a similar impact on CB1 and CB2 receptor endocytosis and therefore understanding the human cell receptor endocytosis response to *cannabis* products can enable anticipating and managing the patient's dose requirements over the time course of treatment with *cannabis*. (See, Ahn, K. H., et al., (2013) "Distinct roles of β-arrestin 1 and β-arrestin 2 in ORG27569-induced biased signaling and internalization of the cannabinoid receptor 1 (CB1)." *J. Biol. Chem.* 288:9790-800; Hsieh, C., et al., (1999) "Internalization and recycling of the CB1 receptor." *J. Neurochem* 73:493-501.

The assay method disclosed herein is used to quantify *cannabis* potency by determining CB1 and CB2 receptor internalization (endocytosis) in response to escalating doses of *cannabis*. Humans will be transfected with either CB1 or CB2 expression plasmids (or both) with distinguishable fluorescent tags for example CB1-EGFP and CB2-mCherry. Receptor endocytosis is not a uniform response in all cells with a population and therefore its detection and quantification require microscopic image analysis equipment and software. Unlike the metric of transduction of *cannabis* through GPCR and G alpha 15/16 which is robust because it is amplified by a cascade of interactions, the metric of receptor endocytosis relies on quantifying fluorescent signals of individual receptors and their cellular localization. For all of these reasons, the analysis output from CB1 and CB2 endocytosis assay can be weak and variable. The assay only should be used as a secondary quantitative method and for confirmation of findings from the $EC_{50}$ Reporter assays.

The $IC_{50}$ Endocytosis Reporter assay comprises human cells transfected with expression plasmids with cDNAs encoding chimeric fluorescent CB1, CB2 or both. Expression plasmids are transfected into cells using commercially available transfection reagents (example, GeneJuice, EMD Millipore). Chimeric constructs for studying cellular localization of the proteins have been published. (See, Bennett, R. P., et al., (2008) "Nuclear Exclusion of the HIV-1 Host Defense Factor APOBEC3G Requires a Novel Cytoplasmic Retention Signal and Is Not Dependent on RNA Binding." *J. Biol. Chem.* 283:7320-27; Bennett, R. P., et al., (2006) "APOBEC-1 and AID are Nucleo-cytoplasmic Trafficking Proteins but APOBEC3G Cannot Traffic." *Biochem Biophys Res. Commun.* 350:214-219; Galloway, C. A., et al., (2010) Biochem. Biophys, Res. Commun. 398:38-43; Miller, H. J. et al., (2007) "The dimerization domain of HIV-1 viral infectivity factor Vif is required to block virion incorporation of APOBEC3G." *Retrovirology* 4:81-91; and Bennett, R. P, et al., (2016) "An analog of camptothecin inactive against Topoisomerase I is broadly neutralizing of HIV-1 through inhibition of Vif-dependent APOBEC3G degradation," *Antiviral Res.* 136:51-59 For example, EGFP (Excitation/Emission wavelengths: 488 nm/509 nm) and mCherry (Excitation/Emission wavelengths: 587 nm/610 nm) are produced as either an N-terminal or C-terminal addition to either CB1 or CB2 to produce chimeric proteins. The fluorescence of these proteins are in direct proportion to the amount of protein expressed and the localization of CB1 and CB2 before and after *cannabis* treatment can be quantified using a fluorescence microscope and image analysis software. Receptors such as CB1-EGFP or CB2-mCherry located on the surface of cells will fluoresce at the plasma membrane of cells and appear as a fluorescent 'ring' circumscribing cells. The fluorescence of this ring will diminish upon receptor endocytosis, giving way to a uniform fluorescence in the cell cytoplasm with punctate brighter spots. Image software analysis quantifies the proportion of fluorescent tagged chimeric CB1 or CB2 appearing at the cell surface relative to the amount of fluorescence within the cells interior, and mathematically calculates from the fluorescence intensity in each location as the proportion of membrane associated receptor and endocytosed receptor by equations #3 and #4 respectively. In the examples of CB1-EGFP and CB2-mCherry gene transfected cells, puromycin antibiotic will be used to select and enrich for cells that have chromosomally integrated the genes (stable cell expression) along with the plasmid encoding gene for resistance to puromycin. Cell clones with maximal fluorescence will be selected by sterile flow cytometry sorting followed by selection in microtiter dishes to limiting dilution of a single clone. The clones are then grown in bulk and frozen as stocks or long-term storage.

Figure 5:
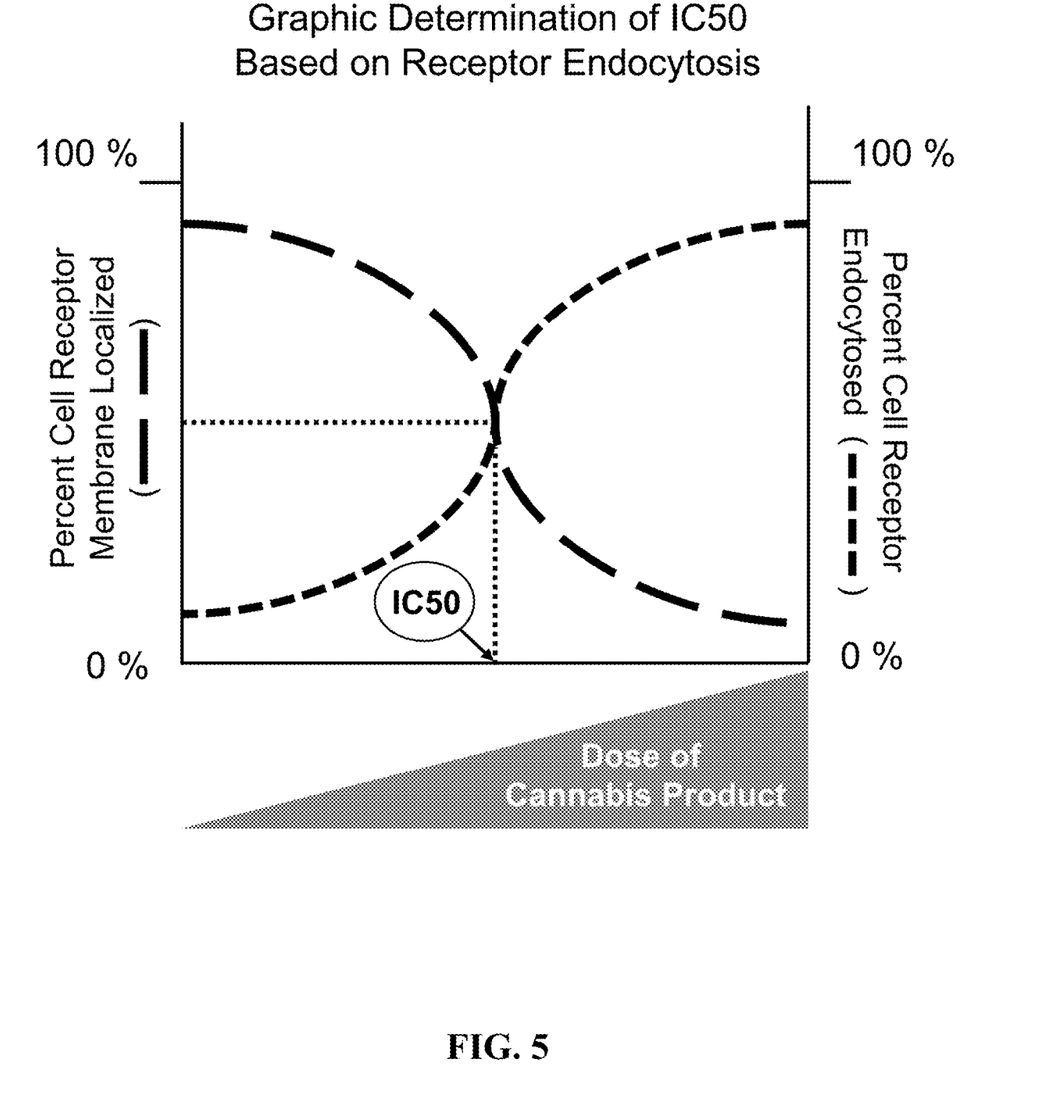
FIG. 5 represents a graph of the dynamic change in specific receptor localization within the membrane or endocytosed in response to escalating doses of *cannabis* product calculated as the 50% inhibitory concentration ($IC_{50}$).

The dynamic change in specific receptor localization within the membrane or endocytosed in response to escalating doses of *cannabis* product can be represented by the dose required for 50% of the maximum receptor endocytosis (or inhibition of *cannabis* signaling through a specific receptor) and calculated as the $IC_{50}$ and visualized graphically as the first derivative of a curve resulting from plotting the data resulting from equation #3 or #4 (on the y axis) vs dose of *cannabis* as per FIG. 5.

$$\text{Fluorescence Intensity}_{membrane} \div (\text{Fluorescence Intensity}_{membrane} + \text{Fluorescence Intensity}_{interior}) \times 100 = \% \text{ of specific receptor remaining exposed at the surface of cells.} \quad \text{Eq. 3}$$

$$\text{Fluorescence Intensity}_{interior} \div (\text{Fluorescence Intensity}_{membrane} + \text{Fluorescence Intensity}_{interior}) \times 100 = \% \text{ of specific receptor endocytosed.} \quad \text{Eq. 4}$$

Quantification Using FRET Pairs

Beta 2 arrestin (NM_004312) is a protein that couples GPCRs to intracellular signaling pathways between the membrane bound receptors on the surface of cells and the pathways in the interior of the cell that modulate biochemical pathways and cell physiology. (See, Nguyen, P. T., et al., (2012) "Beta-arrestin-2 regulates cannabinoid $CB_1$ receptor signaling and adaptation in a CNS region-dependent manner." *Biol. Psychiatry* 71:714-24.)

Intracellular protein to protein interactions, including those involving CB1 or CB2 with arrestin are a quantitative metric for the potency of *cannabis* products to induce the endocannabinoid system. The induction of CB1 or CB2 binding to beta 2 arrestin in response to escalating doses of cannabinoids can be quantified using the quenched Forester Resonance Energy Transfer (FqRET). The FRET method involves irradiation a fluorescent donor molecule so as to induce fluorescent light emission (the donor) and in a distance-dependent manner, have an appropriate second molecule (the acceptor) absorbing the emitted fluorescent light and re emit fluorescent light at a different wavelength in a proportionate and quantifiable manner. In FqRET the acceptor absorbs light from the donor but does not emit fluorescent light. Hence, in FqRET designs, when donor and acceptor are in close proximity the fluorescence of the cells become quantifiably dimmer (quenched) in direct portion to the amount of donor and acceptor interaction (e.g. CB1-EGFP and arrestin-REACh2, donor and acceptor pair).

The disclosed methods provide a means for determining the dose-dependent potency for any given *cannabis* product when genetically engineered human cells are used to quantify the biological response to treatments across escalating doses of cannabis product. This biological assessment of potency of cannabis products containing mixed cannabinoids and plant compounds along defined cannabis receptor signaling pathways (CB1, CB2 and entourage receptors) is the most comprehensive method to date of informing producers, patients and physicians of the quality of the cannabis product in terms of its potency, reproducible dosing and likely medical indications for its use. The cell-based potency testing in all its forms and described herein as the $EC_{50}$ array addresses the current deficiencies in cannabis product potency testing (due to the use of plant chemistries as the sole metric for potency). The current method does not and cannot anticipate the biological response of cells within human tissues and consequently fails to anticipate a cannabis product's potency in humans. Potency testing based on chemical composition analysis alone has created uncertainty in the appropriate medical indications of cannabis products that doctors may recommend to their patients and doses that should be used for each indication. The $EC_{50}$ array overcomes these limitations and road blocks that are due to the lack of research and understanding of the all of the biologically active phyto- and endo-cannabinoid compounds, the receptors they bind to and the interactions responsible for the entourage effect associated with the benefits of medical marijuana.

Although the present invention has been described for the purpose of illustration, it is understood that such detail is solely for that purpose and variations can be made by those skilled in the art without departing from the spirit and scope of the invention which is defined by the following claims.

Kits

Disclosed herein is a kit for quantifying the potency and/or efficacy of one or more cannabinoid and/or terpenoid, alone or in combination, said kit comprising the components as disclosed and/or contemplated herein. A non-limiting example of the disclosed kit can be seen in FIG. 2.

In one aspect the kit comprises:

(a) a plurality human cell lines.

(b) a microplate comprising an array of microwells for receiving the genetically altered human cell lines;

(c) instructions on how to use the plurality of human cell lines for use as an assay for quantifying the potency and/or efficacy in cellular response to one or more cannabinoid and/or terpenoid, alone or in combination; and (d) calcium concentration sensitive, cell permeable fluorescent chemistry In one embodiment the cell line comprises human cells engineered to express either human CB1 or CB2 (or chimeric proteins thereof) and a promiscuous recombinant human beta/gamma subunit that enable the otherwise suppression of calcium release by CB receptors to be a stimulation of calcium release due to cannabinoid signaling.

In a further embodiment, the cell line is prepared by the following procedure:

(a) first using CRISPR/cas9 to knock out of CB1 and CB2 genes from a human cell line such as U2OS or HEK293T; and (b) thereafter transfecting (knocking in) human CB1 or CB2 receptors (or chimeric proteins thereof) into these knock out cell lines and coupling the CB1 or CB2 receptors to human beta/gamma subunits that act promiscuously, wherein the coupling of recombinant CB1 or CB2 (which are members of the Go receptors that inhibit calcium signaling) would be, to Gα15 as an example;

(b) optionally a microplate comprising an array of microwells for receiving the genetically altered human cell lines;

(c) instructions on how to use the plurality of human cell lines for use as an assay for quantifying the potency and/or efficacy in cellular response to one or more cannabinoid and/or terpenoid, alone or in combination; and (d) calcium concentration sensitive, cell permeable fluorescent chemistry.

A direct method for quantifying the potency of cannabis products based on GPCR-dependent changes in intracellular calcium concentration, intracellular inositol phosphate accumulation arrestin binding or ERK/MAPK signaling. FIG. 2 depicts a plate of arrayed human cell types representing different tissues in the body. As shown in the dosing triangles at the top, the plates can be treated with an escalating dose of medicinal cannabis product relative to chemical or hormonal standard agonists, typically in triplicate. The disclosed array provides a method and a means for the reproducible assessment of cannabis product potency as a dose response and $EC_{50}$ in cell types from tissues throughout the human body thus capturing the potential medicinal value to the subject.

In addition, test to test reliability is ensured through ratiometric quantification responses to each dose of cannabis relative to that of a known agonist. Edge effects can be avoided by omitting all of columns 1 and 24 and rows A and P.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A cell-based assay for quantifying the potency and/or efficacy of one or more cannabinoids and/or terpenoids present in a test sample, wherein the assay comprises:
  (a) a microplate comprising an array of microwells containing one or more human cell types representing one or more different human tissues, wherein:
    (i) the one or more human cell types are either wild-type for CB1 and/or CB2, or CB1 knockouts, CB2 knockouts, or CB1/CB2 knockouts, and
    (ii) the one or more human cell types are genetically engineered to express a G protein selected from a promiscuous G alpha protein that converts G protein-coupled receptor (GPCR) signaling to a positive cAMP product and calcium release; and
  (b) one or more reagents for quantifying the potency and/or efficacy of the one or more cannabinoids and/or terpenoids present in the test sample, wherein the quantifying is based on measuring GPCR-dependent changes in the one or more human cell types after the test sample is contacted with the one or more human cell types compared with a calibration control.

2. The assay according to claim 1, wherein the GPCR-dependent changes are changes in intracellular calcium concentration in the one or more human cell types.

3. The assay according to claim 1, wherein said array is arranged so that microwells containing cells from the same type of human cells are arranged in one or more rows.

4. The assay according to claim 1, wherein the array provides a means for conducting a plurality of escalating dosages in order to determine the half maximal effective dose or $EC_{50}$ of the one or more cannabinoids and/or terpenoids present in the test sample for each different human cell type.

5. The assay according to claim 1, wherein the one or more human cell type is A549 lung cell.

6. The assay according to claim 1, wherein the one or more human cell type is Caco-2 gastrointestinal cell.

7. The assay according to claim 1, wherein the one or more human cell type is H9 immune cell.

8. The assay according to claim 1, wherein the one or more human cell type is HepG2 liver cell.

9. The assay according to claim 1, wherein the one or more human cell type is Nav1.3 kidney cell.

10. The assay according to claim 1, wherein the one or more human cell type is NGP neuronal cell.

11. The assay according to claim 1, wherein the one or more human cell type is U2OS bone cell.

12. The assay according to claim 1, wherein the one or more human cell types are derived from human biopsied tissues selected from the group consisting of: skin tissue, gastrointestinal tissue, immune tissue, liver tissue, neuronal tissue, bone tissue, muscle tissue, and any other cell type that expresses an endocannabinoid system.

13. The assay according to claim 1, wherein said GPCR-dependent changes are selected from the group consisting of: changes in intracellular calcium concentration, intracellular inositol phosphate accumulation, cannabinoid receptor internalization from the plasma membrane, arrestin binding to GPCR, ERK/MAPK signaling, changes in protein phosphorylation, and cannabinoid receptor redistribution in the one or more human cell types.

14. The assay according to claim 1, wherein the array of microwells comprises one or more microwells that serve as control microwells.

15. The assay according to claim 14, wherein an $EC_{50}$ response of the control microwells to standardize cell endocannabinoid responses is used for comparing the test sample $EC_{50}$ and for normalizing cellular responses being evaluated for one or more test samples to that of the control microwells.

16. The assay according to claim 1, wherein the one or more cannabinoids is selected from the group consisting of: a phytocannabinoid, an endocannabinoid, and a synthetic cannabinoid.

17. The assay according to claim 16, wherein the phytocannabinoid is selected from the group consisting of: 9 delta tetrahydrocannabinol (9ΔTHC), cannabidial (CBD), and cannabinol (CBN).

18. The assay according to claim 16, wherein the standard calibration control or endocannabinoid is selected from the group consisting of: w-6 endocannabinoid (eCB), anandamide (N-arachidonoylethanolamide), and 2-arachidonoylglycerol (2-AG).

19. The assay according to claim 16, wherein the synthetic cannabinoid is selected from the group consisting of: ACEA wherein the CB1 agonist activity is greater than the CB2 agonist activity, AM251 wherein the CB1 agonist activity is greater than the CB2 agonist activity, JWH133 wherein the CB2 agonist activity is greater than the CB1 agonist activity, and AM630 wherein the CB2 agonist activity is greater than the CB1 agonist activity.

20. The assay according to claim 1, wherein the one or more cannabinoids are in the form of a formulation selected from the group consisting of:
  Marinol® (9ΔTHC analog), Syndros® (THC analog), Casemet® (THC analog), Satevex® (9ΔTHC, CBD, CBN extract), and NY State Tinctures® (20 9ΔTHC:1CBD, 1 9ΔTHC:1CBD, and 1 9ΔTHC:20 CBD).

21. The assay according to claim 1, wherein the terpenoid is selected from the group consisting of: camphene, D3 carene, limonene, and myrcene.

22. A human cell line comprising a human cell type that is (i) either wild-type for CB1 and/or CB2 or CB1 knockouts, CB2 knockouts, or CB1/CB2 knockouts, and (ii) genetically engineered to express a G protein selected from a promiscuous G alpha protein that converts G protein-coupled receptor (GPCR) signaling to a positive cAMP product and calcium release.

23. The human cell line according to claim 22, wherein the cell type with knockout CB1 gene and/or CB2 gene is prepared by the steps of:
  (a) knocking out the CB1 gene or the CB2 gene, or both the CB1 and CB2 genes from the human cell type to form a knock out human cell line; and (b) thereafter transfecting a G protein selected from a promiscuous G alpha protein that converts G protein-coupled receptor (GPCR) signaling to a positive cAMP product and calcium release and coupling remaining or transfected CB 1 and/or CB2 receptors to the G alpha protein that converts GPCR signaling to a positive cAMP product and calcium release.

24. A method for preparing a human cell type with wild-type CB1 gene and/or CB2 gene of the human cell line of claim 22 for quantifying the potency and/or efficacy of one or more cannabinoids and/or terpenoids, said method comprising steps of obtaining human cells that are wild-type for CB1, CB2 or both CB1 and CB2, and thereafter transfecting a G protein selected from a promiscuous G alpha protein that converts G protein-coupled receptor (GPCR) signaling to a positive cAMP product and calcium release in the obtained human cells.

25. The method according to claim 24, wherein the cell type is prepared by the steps of:
transfecting a G protein selected from a promiscuous G alpha protein that converts G protein-coupled receptor (GPCR) signaling to a positive cAMP product and calcium release into the human cells that are wild-type for CB1, CB2, or both CB1 and CB2, and coupling the CB1 and/or CB2 receptors to the promiscuous G alpha protein that converts G protein-coupled receptor (GPCR) signaling to a positive cAMP product and calcium release.

26. A kit for quantifying the potency and/or efficacy of one or more cannabinoids and/or terpenoids according to claim 1, said kit comprising:
(a) one or more human cell types according to claim 1;
(b) a microplate comprising an array of microwells for receiving the one or more human cell types; and
(c) calcium concentration sensitive, cell permeable fluorescent dyes.

27. A method for quantifying the potency and/or efficacy of one or more cannabinoids and/or terpenoids, said method comprising:
(a) providing an assay according to claim 1;
(b) introducing one or more cannabinoids and/or terpenoids, into each of the microwells; and
(c) quantifying the potency and/or efficacy of the one or more cannabinoid based on G protein-coupled receptor (GPCR)-dependent increased of calcium in the one or more human cell types after the test sample is contacted with the one or more human cell types as visualized by calcium concentration-sensitive, cell permeable fluorescent dye added to the tissue culture media in each microwell compared with calibration control.

28. The method according to claim 27 further comprising performing the steps of:
(a) thawing frozen cells of known number and adding thawed cells to the microwells of the microplate in a concentration to cover the bottom of each microwell such that 60% of the cells are in direct contact with one another in tissue culture media appropriate to each cell type;
(b) maintaining the cells for 12 to 24 hours to become adherent under cell growth conditions of temperature, humidity and $CO_2$ appropriate for each cell type;
(c) diluting stock solutions of calibration control and test substances in half-log concentration steps from full strength concentration of the stock solutions over 7 dilutions appropriate for adding to the tissue culture media in each well to achieve the desired final concentrations;
(d) incubating the cells with the dilutions of the calibration control and test substance as in Step (c) for varying durations ranging from minutes to hours;
(e) adding calcium concentration sensitive, cell permeable fluorescent dye of appropriate concentrations to each microwell and allowing reaction with cells for minutes to hours;
(f) quantifying fluorescence due to calcium binding to the fluorescent dye by a plate reader at the appropriate excitation/emission light wavelengths; and
(g) calculating $EC_{50}$ based on half maximal fluorescent signal a dose-range assay of the seven dilutions for the calibration control and test substance treatment groups and averaging the triplicate measurements.

29. The method according to claim 28, wherein fluorescent signal of the calibration control and test substance potency and $EC_{50}$ are quantified following discrete steps in the endocannabinoid systems where the cells have been engineered to express fluorescent CB1 or CB2 cannabinoid receptor and internalization of the receptor via the plasma membrane is a dose-dependent response of the endocannabinoid system to cannabinoids treatment.

30. The method according to claim 28, wherein fluorescent signal of the calibration control and test substance potency and $EC_{50}$ are quantified following discrete steps in the endocannabinoid systems where the cells have been engineered to express arrestin and CB1 or CB2 as FRET (Forester Resonance Energy Transfer) pairs to induce intracellular translocation of arrestin and binding to GPCRs.

31. The method according to claim 28, wherein fluorescent signal of the calibration control and test substance potency and $EC_{50}$ are quantified following discrete steps in the endocannabinoid systems where the cells have been engineered to express members of the ERK/MAPK pathway as FRET pairs reporter of potency of the cannabinoid substance for activation of the endocannabinoid system.

32. The method according to claim 28, wherein fluorescent signal of the calibration control and test substance potency and $EC_{50}$ are quantified following discrete steps in the endocannabinoid systems where the cells have been engineered to express reporter genes responding to trans-acting gene transcription factors as reporters of potency of the cannabinoid substance for activation of the endocannabinoid system.

33. The assay according to claim 1, wherein the promiscuous G alpha protein is G alpha subunit 15.

34. The kit of claim 26, further comprising instructions on how to use the one or more human cell types for quantifying the potency and/or efficacy in cellular response to one or more cannabinoid and/or terpenoid, alone or in combination.

* * * * *